United States Patent [19]

Fischer

[11] Patent Number: 4,899,577

[45] Date of Patent: Feb. 13, 1990

[54] DEVICE FOR A HARDNESS MEASURING INSTRUMENT

[76] Inventor: Helmut Fischer, Industriestrasse 20, 7032 Sindelfingen-6, Fed. Rep. of Germany

[21] Appl. No.: 192,623

[22] Filed: May 11, 1988

[30] Foreign Application Priority Data

Nov. 10, 1987 [DE] Fed. Rep. of Germany ....... 3738106

[51] Int. Cl.$^4$ ............................................. B21D 22/14
[52] U.S. Cl. ................................................... 73/82
[58] Field of Search ....................... 73/79, 81, 82, 818, 73/823, 150 R; 118/712; 427/8, 9; 310/14, 13

[56] References Cited

U.S. PATENT DOCUMENTS

| | | | |
|---|---|---|---|
| 3,202,886 | 8/1965 | Kramer | 310/14 |
| 3,425,263 | 2/1969 | Elliott et al. | 73/79 |
| 4,094,188 | 6/1978 | Belloon et al. | 73/81 |
| 4,111,039 | 9/1978 | Yamawaki et al. | 73/81 |
| 4,542,311 | 9/1985 | Newman et al. | 310/13 |
| 4,611,487 | 9/1986 | Krenn et al. | 73/81 |
| 4,671,104 | 6/1987 | Fischer | 73/81 |
| 4,691,559 | 9/1987 | Fischer | 73/81 |

FOREIGN PATENT DOCUMENTS

| | | | |
|---|---|---|---|
| 603531 | 10/1934 | Fed. Rep. of Germany | 73/81 |
| 0676908 | 8/1979 | U.S.S.R. | 73/81 |
| 1040382 | 9/1983 | U.S.S.R. | 73/81 |

Primary Examiner—Robert R. Raevis

[57] ABSTRACT

A bar device has one end portion supporting a test body and is pivotable about a pivot center. The bar device comprises a measuring device together with a probe, which works on the basis of measuring the thickness of thin layers. An energizing means acts on the bar device and comprises a first part rigid with a housing and a second part rigid with the bar device. A geometric first longitudinal axis passes through the center of the probe and the center of the test body. The part rigid with the housing comprises a cylindrical electromagnetic coil having a geometric second longitudinal axis parallel with the first longitudinal axis. The coil has a clear space parallel with the second longitudinal axis. Substantially coaxial with the second longitudinal axis, a carrier rod is rigid in its longitudinal direction relative to the end portion of the bar device and is connected in entraining fashion to the bar device. The carrier rod carries an upper magnet carrier above the coil and a lower magnet carrier below the coil. Fixed to the magnet carriers are rigid permanent magnets of which one pole points axially in the same direction. The travel of the carrier rod amounts to a few millimeters.

16 Claims, 6 Drawing Sheets

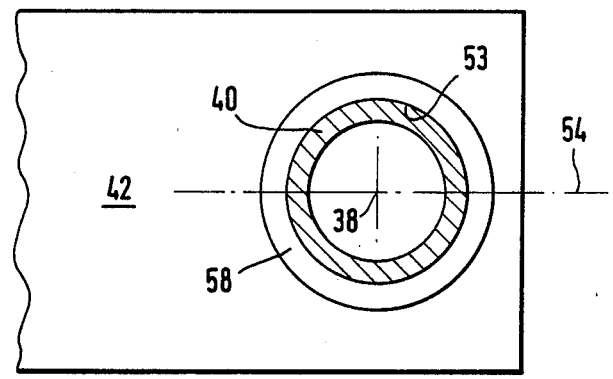
FIG.4
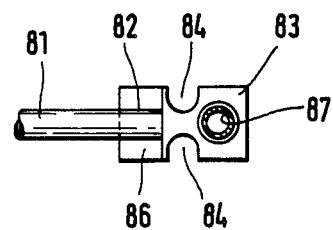
FIG.5
FIG.6
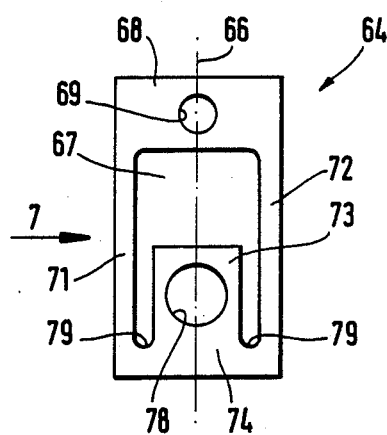
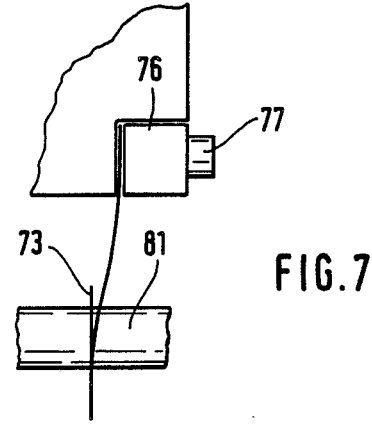
FIG.7

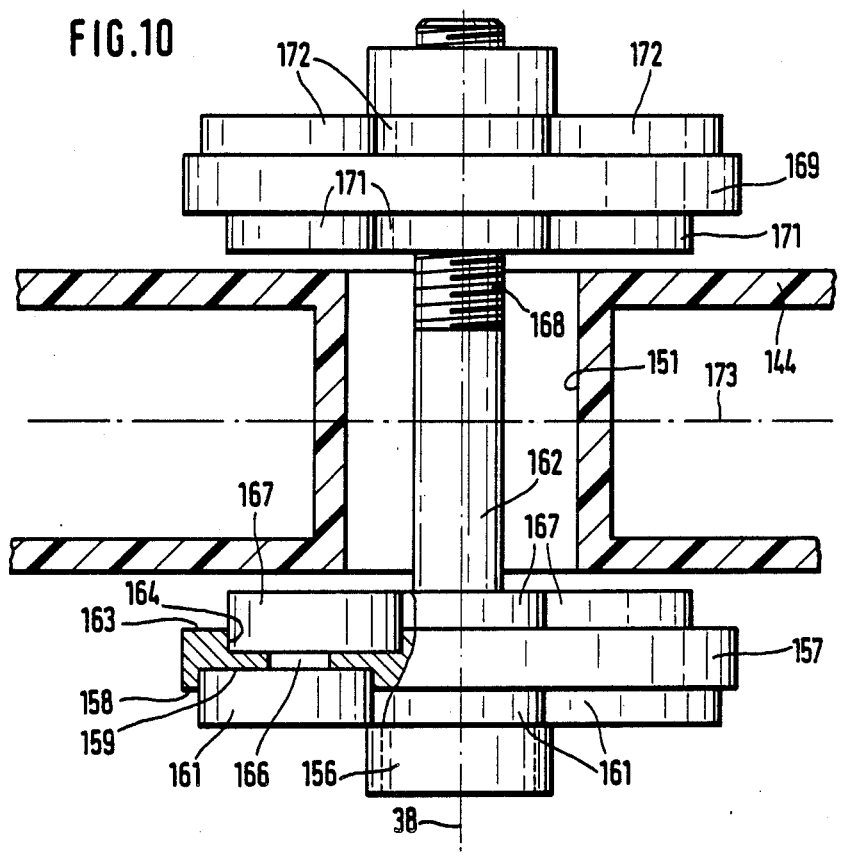
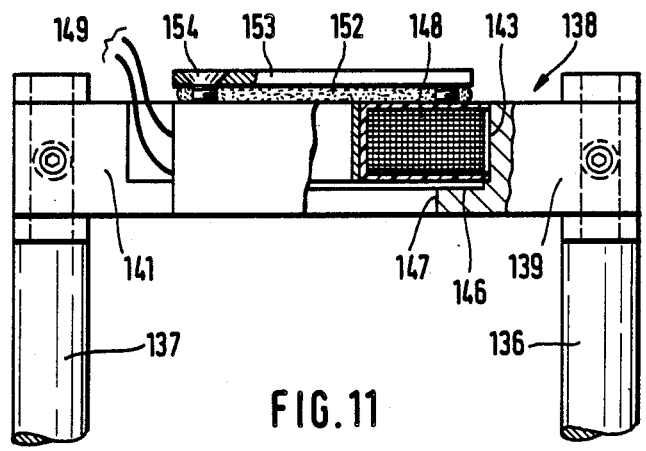

DEVICE FOR A HARDNESS MEASURING INSTRUMENT

The invention relates to a hardness measuring instrument that employs a measuring device that works on the basis of probes for measuring the thickness of thin layers.

BACKGROUND OF THE INVENTION AND RELEVANT PRIOR ART

Such a device is known from German published specification No. 35 01 288 (U.S. Pat. No. 4,691,559, English patent specification No. 58 03 109 and Japanese Patent Application No. 87647/85).

It shows a test body 67 and a bar device around and in the transverse plane 21. The measuring device 74 measures on the basis of probes for measuring the thickness of thin layers. The rotor of an energizer 31 is pivotable about a pivot center while a stator is rigidly connected to the plate 16 belonging to the housing. A first geometric longitudinal axis lies in the transverse plane 21. This is the vertical axis 54.

A similar device is also described in German published specification No. 34 08 554 (U.S. Pat. No. 4,671,104, English Pat. No. 21 55 639 and Japanese published specification No. 75655/84).

Where these devices are concerned, the bar device or at least a part of the bar device is connected to the housing via a pivot bearing. So that they can rotate, such pivot bearings must in any case have some clearance, whatever form it may take. This limits the accuracy of the measuring device. Furthermore, the bar device is connected to the energizer by a further very long bar device (or by an arm 37 in the case of DE-OS 35 01 288). This has various disadvantages. For example, the housing is longer by this length. The current noise in the winding 136 is amplified by the lever ratio. The term current noise is meant to imply that the coil current cannot always be kept constant, for various reasons.

The result of measurement is also adversely affected in that the arm 37 is subject to bending. If it is desired to prevent this bending, then it must be made very thick in the bending direction, which entails mass, so that the measuring system becomes more sluggish and the instrument becomes heavier and also any transit locking devices have to be more rugged.

Furthermore, it is to a certain extent a problem to generate a linear force.

Devices, therefore, according to the relevant prior art include
a housing,
a bar device having an end portion and pivotable about a pivot center,
a test body and a probe supported on the end portion,
a measuring device which works on the basis of probes for measuring the thickness of thin layers,
an energizing means acting on the bar device having a first part rigid with the housing and a second part rigid with the bar device, and
a geometric first longitudinal axis passing through the center of the probe and the center of the test body.

OBJECT AND STATEMENT OF THE INVENTION

The object of the invention is to avoid all the aforementioned disadvantages. Nevertheless, it should be possible in principle to continue to work on the same idea as before. In particular, it should be possible to continue to utilize the linearity relationship such as is shown, for instance, in FIG. 11 or 12 of German published specification No. 35 01 288.

According to the invention, this object is achieved by the following features:

(a) The first part rigid with the housing comprises a cylindrical electromagnetic coil having a geometric second longitudinal axis parallel with the geometric first longitudinal axis, (b) The coil has a clear space parallel with the geometric second longitudinal axis, (c) Substantially coaxial with the geometric second longitudinal axis there is a carrier rod which is rigid in its longitudinal direction relative to said bar device and which is connected in entraining fashion to the bar device, (d) The carrier rod carries an upper magnet carrier above the coil and a lower magnet carrier below the coil, (e) Fixed to the magnet carriers are rigid permanent magnets each having one pole that points in the same direction, and (f) The travel of the carrier rod amounts to a few millimeters. Where this device is concerned, the force is proportional to the current 1 used to energize the coil. The ohmic resistance of the coil is immaterial because an impressed current is used. Therefore, the temperature coefficient of the coil is also negligible. There should be no iron around the coil unless it is material intended to provide a screen against interference fields such as is possible with Mu metal.

The device contributes to a reproducibility of 0.1 milli-Newtons and the forces can increase from 0.1 milli-Newtons to 1 Newton. It helps to provide a resolution of 2 to 3 nanometers. It is well known that 2 nanometers correspond to about 20 atoms diameter.

The following additional features are described with respect to a preferred embodiment.

The coil is an air coil. As a result, it is possible to ensure that apart from the action of the permanent magnets, no other unintended magnetic effect occurs.

The coil has 1000 to 2000 turns of a copper wire less than 1 mm in diameter. The coil occupies relatively little space, is sufficiently light and can apply the necessary forces under fine control.

The coil is designed for currents at least in the range from 0.5 amps to 40 uA. Details of a possible heat dissipation and other operating data are obtained, indicating how the coil should be constructed.

The coil is embedded in a solid rigid transverse yoke having two oppositely disposed marginal portions connected each to a solid column, the column having ends rigidly connected with the housing, and this arrangement is virtually rigid for the measurement forces which occur. These features make it possible to avoid the coil tilting and a symmetrical arrangement is obtained which can accommodate the forces for which is virtually rigid.

The first and second longitudinal axes are aligned with each other. This provides a direct action of the energizer on the test body without any circumventing levers, transmissions or such like which would eat up any clearance and/or might well cause one another to bend.

The carrier rod is composed of light metal. This provides a saving on weight, avoids inertia and avoids the occurrence of undesired magnetizing units.

The carrier rod forms a rigid continuation of the bar device. This provides a virtually monolithic connection between the test body and the movable part of the energizer.

Each of the magnet carriers has top and bottom ends and carries the like-poled permanent magnets both at the top end and the bottom end. This means that the magnet carrier can be smaller in diameter and the magnetic effect will be increased.

All of the permanent magnets are the same and each of the magnet carriers has the same magnetic force. This means that only one type of permanent magnet is required and a symmetry is obtained with regard to the central plane between the permanent magnets of the two magnet carriers.

The number of permanent magnets is the same on all magnet carriers. This means that only the number of permanent magnets need to be made the same and one will then automatically arrive at the same magnetic force without having to carry out any secondary measurement to ascertain whether the magnetic force is the same.

The permanent magnets are of the KOERMAX type (registered trade mark of Messrs. Friedrich Krupp GmbH). Magnets of the type have been very successful. These are anisotropic rare earth magnets.

The permanent magnets have a diameter in the region of 6 mm, a height in the region of 2 mm and 2×4 of them are provided on each of the magnet carriers. This provides small constructions which can easily be accommodated on circles.

The magnet carriers having matching depressions, and over a part of their height the permanent magnets are glued into the matching depressions and the glue is a cold hardening adhesive. This means that the permanent magnets do not shift when they are fitted and always assume their predetermined place.

The transverse yoke is non-magnetizable. This makes it possible to avoid having iron particularly in the region of the coil.

The columns are non-magnetizable. This makes it possible to avoid having iron along the bar device also.

DESCRIPTION OF THE DRAWINGS

The invention will now be described with reference to a preferred embodiment shown in the accompanying drawings, in which:

FIG. 4 is a section taken on the line 4—4 in FIG. 1;

FIG. 5 is a section taken on the line 4—4 in FIG. 1;

FIG. 6 is a view of a leaf spring which serves as a pivot joint;

FIG. 7 is a view according to the arrow 7 in FIG. 6, partly broken away to illustrate the effect of the leaf spring in FIG. 6;

FIG. 10 is a partly broken away view of the carrier rod with the magnet carriers and permanent magnets and with the broken away bobbin carrier, and FIG. 11 is a view according to arrow 11 in FIG. 9, without the housing walls, partly broken open.

DESCRIPTION OF A PREFERRED EMBODIMENT

Figure 1:
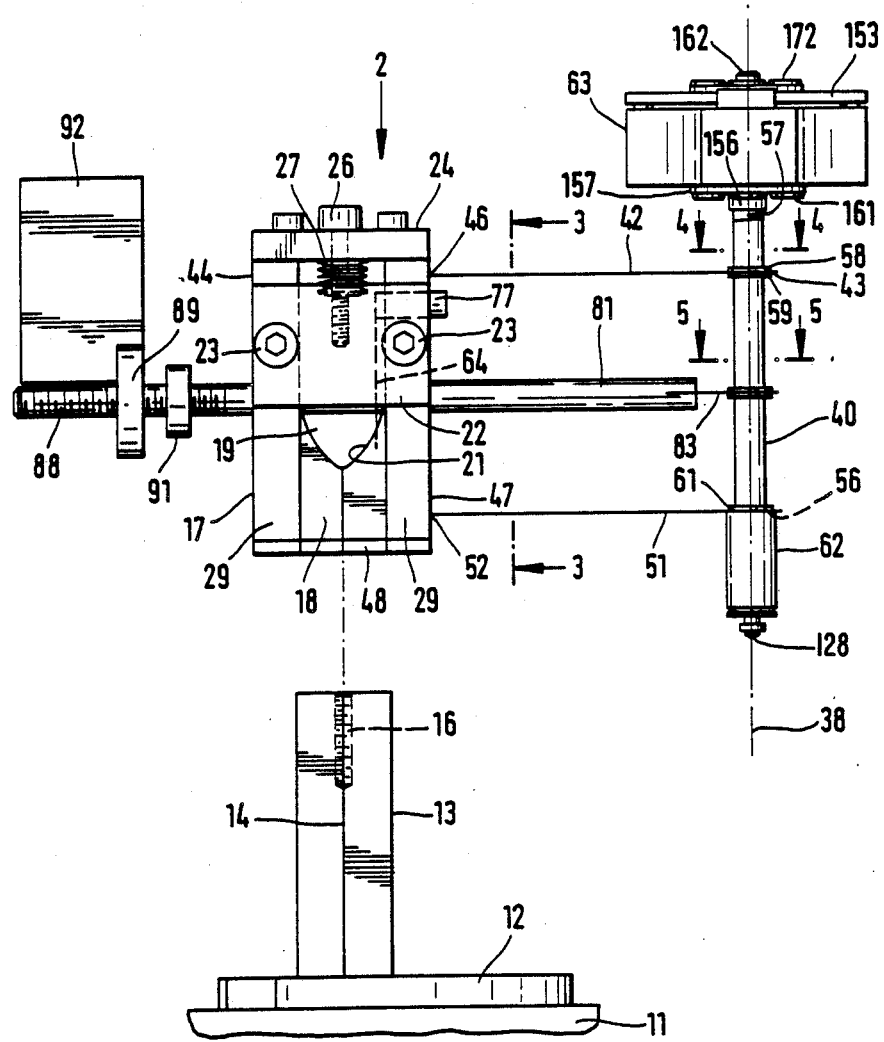
FIG. 1 is a partly exploded side view of the device according to the invention.
Figure 2:
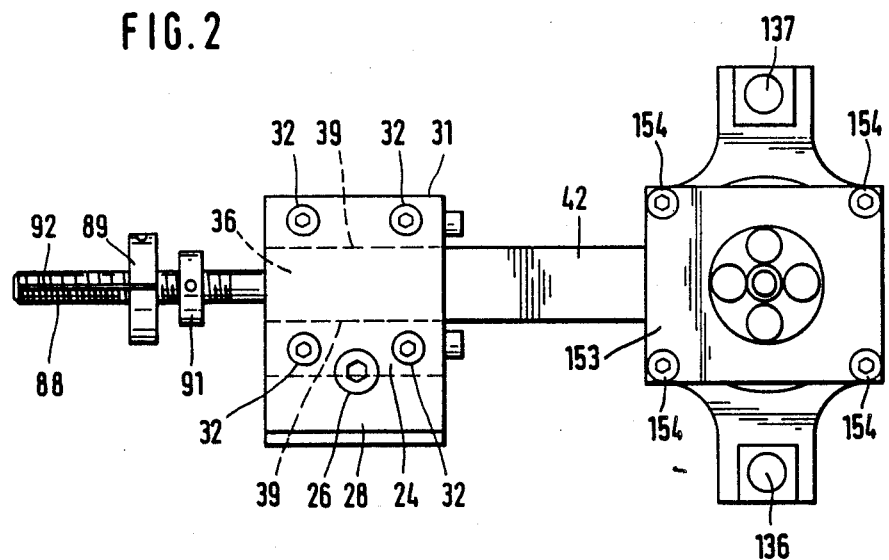
FIG. 2 is a view according to the arrow 2 in FIG. 1.
Figure 3:
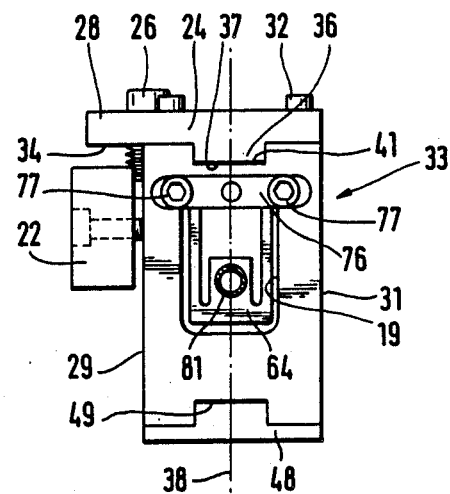
FIG. 3 is a section taken on the line 3—3 in FIG. 1.
Figure 9:
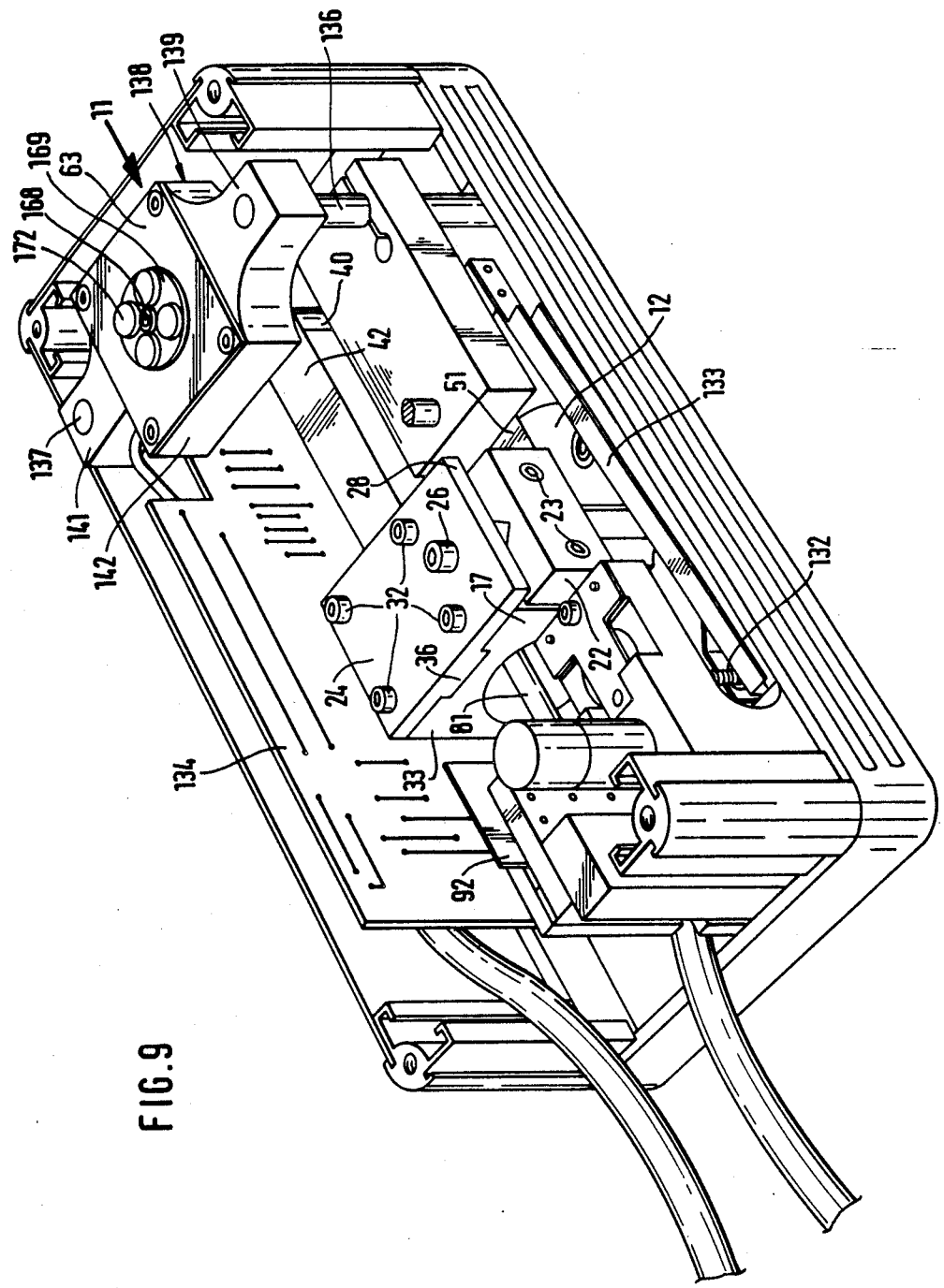
FIG. 9 is a perspective overall view of a hand instrument, partly opened.

Screwed onto the bottom 11 of a hardness measuring instrument shown in FIG. 9 is a carrier plate 12 on which a stand 13 is fixed which has a quadratic cross-section and of which one edge 14 is facing forwardly in FIG. 1. Extending within it from an end face is a blind screwthreaded hole 16. Corresponding to the square cross-section of the stand 13, a triangularly prismatic guide 18 is incorporated into a metallic bearing block 17 from the latter's front face and intersects a longitudinal recess 19 (FIG. 3), which is why the lines of intersection 21 are shown in FIG. 1. A clamping block 22 is secured by screws and has a recess matching the guide 18 so that the square cross-section of the stand 13 can be accommodated and almost completely enclosed when the screws 23 are tightened, the stand 13 being clamped securely so that it is no longer displaceable in the direction of its height. The bearing block 17 comprises an upper clamping plate 24 in which there is a through bore aligned with the bind threaded hole 16. Between the under side of the clamping plate 24 and the upper end face of the stand 13 there is clamped a set of spring washers 27. As the screws 23 are slackened, the bearing block 17 moves down the stand 13 or upwards if the screw 26 is turned in the other direction. For the set of plate springs 27 and the screw 26, the clamping plate 24 has a projection 28 pointing to the left in FIG. 3 and which extends beyond the flat surface 29 shown on the left in FIG. 3. Close to the surface 29 and the flat surface 31 on the bearing block 27 which is parallel with it, the clamping plate 24 has four through bores to receive four screws 32 which are screwed into a member 33 which, as shown in FIG. 3, is shaped like a compressed H and which forms the core of the bearing block 17. Extending over its flat under side 34 and always at a right-angle to a geometrical longitudinal axis 38 of a small tube 40 which will be discussed later, the clamping plate 24 has a projection 36. The lateral flanks 39 of the projection 36 extend parallel with one another and vertically in the view shown in FIG. 3. According to FIG. 3, complementary to this configuration, the member 33 has a broad flat groove 41 disposed centrally and also perpendicular to the geometric longitudinal axis 38. Between the under side 37 and the bottom of the groove 41 is clamped the (according to FIG. 1) left-hand portion of a first leaf spring 42 which consists of beryllim/-copper. The full scale drawing in FIG. 1 shows the front end 43 of the leaf spring 42. The rear end 44 is aligned with the back of the bearing block 17, producing a clamping area about 3 cm long which is very long in comparison with the overall length of the leaf spring 42 which is 88.5 mm. The emergence 46 of the leaf spring 42 from the bearing block 17 lies clearly in the flat side 47 which is on the right in FIG. 1 and which extends parallel with the geometric longitudinal axis 38. At the emergence 46 the projection 36 and the bottom of the groove 41 are sharply edged so that there is a clearly defined emergence 46, a clearly defined clamping effect and a clearly defined gap in respect of the geometric longitudinal axis 38. The leaf spring 42 is 0.1 mm thick, which is why it cannot be seen in the view in FIG. 3 which is likewise a full-scale drawing. It is 12 mm wide and the groove 41 is only a little wider so that it can accommodate the leaf spring 42 without any clamping. As FIG. 3 shows, the under side 37 and the bottom of the groove 41 are at right-angles to the geometric longitudinal axis 38.

Screwed to the under side of the body 33 is a clamping plate 48 which, except for the projection 28, is identical to but somewhat thinner than the clamping plate 24. By means of it and the groove 49 directed in opposition to the groove 41, an identical second leaf spring 51 is secured. Since the circumstances have been accurately described with reference to the leaf spring 42, they need not be repeated here. It should merely be pointed out that also this groove 49 must extend at right-angles to the geometrical longitudinal axis 38 and that the point of emergence 52 is at the same distance from the geometric longitudinal axis 38. Also the leaf spring 51 is of Cu Be 2 and is 0.1 mm thick. The other dimensions are also completely identical. The leaf springs 42, 51 are absoltely flat and have no inherent tension which might originate from unsuitable machining processes or from any bulges in them. The homogeneity of the properties is also assured in respect of forces of 0.1 to 0.01 milli-Newtons.

In its free end zone, the leaf spring has a circular hole 53 6 mm in diameter. This, too, has been produced without stress at the edges, by etching. The hole 53 is both coaxial with the geometric longitudinal axis 38 and also exactly in the median line 54 of the leaf spring 42. By reason of this latter, there is no tendency to tilt. The leaf spring 51 comprises a hole 56 having exactly the same geometry.

The small tube 40 consists of a titanium/aluminium alloy so that it is both light and also rigid. It is produced by being cut from the solid. Its outside diameter corresponds to the diameter of the holes 53, 56. In the position of rest (neutral position), the small tube 40 is exactly coaxial with the geometric longitudinal axis 38. At the top, it has an external screwthread 57. The tube 40 is fitted into the hole 53 both by a small ring 58 being pushed on from above and also by a small ring 59 pushed on from the bottom. These separate rings are fastened to the tube 40 by a cold-setting glue. In the lower portion, at the height of the top of the leaf spring 51, the tube 40 has a circularly cylindrical shoulder 61, the under side of which is spaced apart from the right-hand end portion of the leaf spring 42 by exactly the same amount as the gap between the points of emergence 46 and 52. Under the shoulder 61, the tube 40 traverses the hole 56 and projects a little farther downwards so that it fits into a coaxial sleeve 62. To the upper portion of this sleeve 62 and the shoulder 61, a little cold setting adhesive has been applied. "Cold" in this case naturally means a temperature which does not alter the structure of the leaf springs. Right at the bottom, the sleeve 62 grips a diamond 128 which constitutes the test body and screwed onto the external screwthread 57 is a coaxially arranged electric motor drive unit 63. This configuration would be adequate if one were sure that the geometric longitudinal axis 38 would always point to the centre of the earth during measurement. However, in order to be able to measure in any desired position, further measures are adopted: a leaf spring 64 is shown in FIG. 6 to a scale of 2:1. It is 14 mm wide, 25 mm high, is likewise made from Cu Be 2, is 0.1 mm thick and is given its shape by etching, without stress. It is completely flat when at rest. Its median plane 66 is also simultaneously in the geometric longitudinal axis 38 and the median line 54. It is symmetrical with the median plane 66. Its plane which is in the plane of the drawing in FIG. 6 is parallel with the geometric longitudinal axis 38. The (in plan view) rectangular leaf spring 64 has in it a centrally symmetrical cut-out 67 of an upside-down U-shape. Above this is a broad clamping zone 68 with a positioning hole 69 from which two narrow arms 71, 72 extend downwardly on either side. Separated from these by the longitudinal arms of the U is a central tongue 73 which merges at the bottom and via a cross web 74, into the arms 71, 72. Where the corners of the cut-out 67 may during operation be exposed to stress, a radius of 0.75 mm is provided. The leaf spring 64 is clamped in the longitudinal cut-out 19 by a clamping plate 76 in stress and curvature-free manner so that it hangs in a vertical direction, the clamping force being applied by two screws 77. The positioning hole 69 is traversed by a positioning stud (not shown) which is rigidly connected to the member 33. As FIG. 6 shows, the boundary edges of the leaf spring 64—in so far as they extend vertically—run parallel with the geometric longitudinal axis 38 or at right-angles to the latter if they extend horizontally. Etched centrally into the central tongue 73 is a circular hole 78, the central axis of which intersects the geometric longitudinal axis 38. The radii 79 are substantially lower down than the bottom edge of the hole 78 and are at least 2 mm away from the bottom edge so that the middle tongue 73 can, according to FIG. 7, when standing approximately vertically, move leftwards when a force at the hole 78 exerts a force directed leftwardly in FIG. 7. The arms 71, 72 then extend in a slight S-shape. This force can be applied by a second tube 81 which passes through the hole 78 being fixed rigidly therein by the above-mentioned adhesion technique. For reasons of weight and rigidity, the tube is likewise made from an aluminium-titanium alloy and is thin-walled. Its outside diameter is 5 mm and it is about 11.5 cm long. Its end portion which is on the right in FIG. 1 has a short transverse slot 82 which lies exactly in the plane of the leaf springs 42, 51, which means at a right-angle to the geometric longitudinal axis 38. A leaf spring 83 which is short in comparison with the leaf springs 42, 51 but is just as wide and consists of the same materials, and which is stress free in the position of rest and which has been etched in its contours has, as shown in FIG. 5, two deep lateral depressions 84 between which remains roughly one-quarter of the width of the leaf spring. To the left of this there remains a fin 86 which is glued without stress into the slot 92. As FIG. 1 shows, the right-hand end of the tube 81 is at a slight distance of about 8 mm from the geometric longitudinal axis 38. The leaf spring 83 is exactly at right-angles to the geometric longitudinal axis 38 and has a hole 87 corresponding to and completely flush with the holes 53, 56. By means of the same technique of small rings or mating flange in one piece with the tube 40, adhesive fixing is carried out in the peripheral zone of the hole 87.

The tube 81 has on the left and external screwthread 88 onto which is screwed a counterweight 89 with a locking nut 91. Furthermore, there is on the external screwthread 88 a disc 92 for an electric damping device, the functioning of which is of no interest here. The counterweight 89 can be used to achieve such a fine equalisation of weights that with the configuration shown in FIG. 1 there is no flexion of the leaf springs 42, 51, 83.

Figure 8:
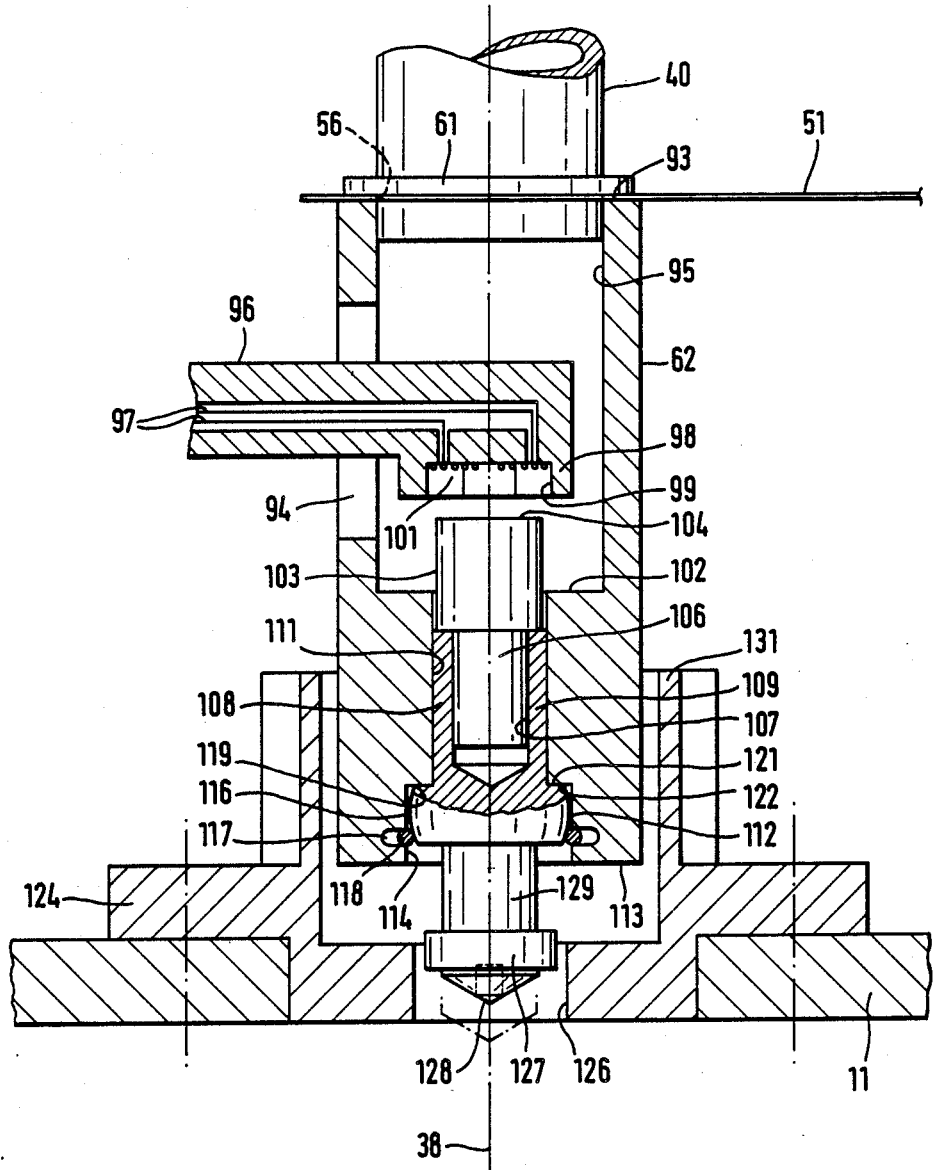
FIG. 8 is a section through the right-hand bottom area of the tube shown on the right in FIG. 1.

According to FIG. 8, which of course is shown to a scale of 10:1, we see at the top the tube 40 which is of 6 mm diameter. The sleeve 62 is secured by cold setting adhesive, in this sequence: collar 61 against the underside of which bears the leaf spring 51, the upper coaxial circularly cylindrical end face 93 of the aluminium sleeve 62 and the overlapping insertion of the very bottom portion of the tube 40 into an upper coaxial bore 95 of a farther downwardly extending stepped bore. According to FIG. 8, from the left, and according to FIG. 1, from the right, the sleeve 62 has in the remaining wall a large hole 94 into which projects an arm 96 rigid with the housing and in which there are electrical supply conductors 97 which lead to a probe head 98 which is comparable with the probe 77 in the Published Specification mentioned at the outset. In the coil space 99 coaxial with the geometric longitudinal axis 38 there is, as indicated, a coil 101. The bottom 102 of the bore 93 is considerably lower down than the bottom of the coil 101. Projecting upwardly from it is a measuring terminal 103 which consists of Al Cu Mg Pb F 38. Its end face 104 is finely finished and is at a right-angle to the geometric longitudinal axis 38. Its stud 106 fits securely in a bore 107 in a rotationally symmetrical diamond carrier 108. Its sleeve 109 fits in a coaxial continuation bore 111 which is not touched by the head of the measuring terminal 103. In the region below the end of the bore 107, the diamond carrier 108 has a convex bead 112 which projects outwardly. The bead 112 fits in a flat circularly cylindrical bore 114 which ends at the bottom end face 113 of the sleeve 62. The bore 114 has in its wall below the thickest point 116 of the bead 112 an inner peripheral groove 117 which extends at a right-angle to the geometric longitudinal axis 38 and in which there fits a snap ring 118 which in its position closer to the relaxed position projects at least partially into the bore 114 while in its completely relaxed position it does not project any farther therein than that corner 119 formed by the periphery of the bead 112 and a circular shoulder 21 which is at right-angles to the geometric longitudinal axis 38 and which forms on the inside the transition with the peripheral surface of the sleeve 109. This shoulder 121 lies on the bottom 122 of the bore 114, in fact in clearly defined fashion, being also securely held in this position by the snap ring 118 which is subject to tension and which—since it is slipped over the thickest point 118—seeks to push the bead 112 upwardly and with it the entire diamond carrier 108.

Disposed in the housing bottom 11 and shown in FIG. 8 is the insert 124 which comprises a central bore 126 through which the mount 127 of a diamond 128 can pass. Via a cylinder 129, the mount 127 is in one piece with the bead 112. The insert 124 also has a pot-shaped part 131 which is open at the top, prevents movements in an undesired direction and so protects the bottom part of the sleeve 62 and the diamond carrier 108. This construction makes it possible to measure coaxially in the immediate vicinity of the diamond 128 and permits of a very simple but reproducible interchangeability of the diamond carrier 108. The end face 104 follows almost directly (for practical purposes absolutely directly) the movement of the diamond 128 and of its tip. The end face 104 corresponds to the downwardly facing surface of the part 74 mentioned in the German published specification already mentioned at the outset.

FIG. 9 shows the disposition of the device according to the invention. The spindle 132 and the leaf spring 133 correspond to the spindle 104 and the leaf spring 96 in the German published specification. Any necessary electronics are mounted on a circuit board 134.

If the measuring terminal 103 is of aluminium, then from the point of view of forces, there is no retroaction between it and the coil 101. However, if it is as preferred produced entirely or at least in its upper part from ferrite, then there is a substantially better sensitivity of the indication. No retroaction could be measured with ferrite, either.

The centre of gravity of all masses acting on the tube 81, including its own mass, lies in the hole 78.

Two equally long columns 136, 137 are parallel with each other and have their bottom ends rigidly connected to the bottom 11. They are symmetrical and parallel with the geometric longitudinal axis 38 and with the central plane 66. The columns 136, 137 are not shown in FIG. 1. At their top ends, they are rigidly connected to a brass transverse yoke 138 which is stepped in respect of its body 142 by two lugs 139, 141. The distance between the columns 136, 137 is about 6.5 cm. The body 142 is about 12 mm thick. Coaxial with the geometric longitudinal axis 38, there is in the body 142 a stepped bore, the larger step 143 accommodating a coil carrier 144 which at the bottom rests on a circular moulding 146. The step 147 of the stepped bore has a smaller diameter than the step 143. In the coil carrier 144 which is of synthetic plastics material, there is a coil 148, the connections 149 of which are led outwards. The coil carrier 144 has an aperture 151 coaxial with the geometric longitudinal axis 38. The coil 144 is radially immovable in the step 143. At the bottom, it rests on the moulding 146. At the top, it is covered by a disc-shaped foam layer 152 having a hole corresponding to the aperture 151. The layer of foam 152 is covered by a clamping plate 153 of aluminium having in its four corners apertures through which pass screws 154 which are screwed into the body 152 so that the coil carrier 144 is pressed gently but securely downwardly.

In so far as they have been described, the parts 136 to 154 are absolutely rigid with the housing and resistant to the forces which arise.

Screwed onto the external screwthread 57 is an internally screwthreaded sleeve 156 which is one piece with a circularly disc-shaped bottom magnet carrier 157. Machined into the magnet carrier 157 from its underside 158 are four cup-shaped circular depressions 159, their central point lying on a common diameter and which are offset by in each case 90°, or are at identical angular distances from one another. Glued into them are identical permanent magnets 161 6 mm in diameter and 2 mm high. They project considerably below the under side 158. At the top, the magnet carrier 157 is coaxial with the geometric longitudinal axis 38 and merges into a carrier rod 162 of aluminium which is 3.2 mm in diameter. Provided on the upper side 163 over the depressions 159 are depressions 164 of the same shape, likewise four in number but located on a smaller diameter around the geometric longitudinal axis 38, since this is permitted by the smaller diameter carrier rod 162. The depressions 159, 164 are connected to one another by a connecting bore 166. Glued into the four depressions 164 are permanent magnets 167. Both the permanent magnets 161 and also the permanent magnets 167 have their south pole directed downwardly. The carrier rod 162 traverses the aperture 151 and has an external screwthread 168 at its top end. Screwed onto this is a coaxial magnet carrier 169 which has the same outside diameter as the magnet carrier 157, in other words 19 mm. In the same way, this magnet carrier 169 has bottom magnets 171 and top permanent magnets 172. The disposition of the permanent magnets 171, 172 is symmetrical in relation to the central plane 173 of the coil. The magnet carrier 169 has the same depressions and connecting bores as the magnet carrier 157 but in a mirrored opposite situation on the central plane 173 of the coil.

The invention makes it possible to make the force exactly proportional to the electric current. This is true at least up to an overall travel of the movable part of the energiser of 4 mm. However, a travel of only 1 to 2 mm is required in the instrument. At the actual time of measurement, the travel from position of rest to application of the diamond to the object measured is only 0.1 mm.

What is claimed is:

1. A non-destructive microhardness measuring instrument comprising
   a housing,
   a bar device having an end portion and pivotable about a pivot center,
   a test body supported on said end portion,
   a measuring device, which works on the basis of measuring the thickness of micro-thin layers, including a probe fixed to the housing and means defining a reference plane for measuring the distance to the probe fixed to the test body,
   an energizing means acting on said bar device having a first part rigid with said housing and a second part rigid with said bar device,
   a geometric first longitudinal axis passing through the center of said probe and the center of said test body,
   and the improvement wherein:
   (a) said first part of said energizing means rigid with said housing comprises a cylindrical electromagnetic coil having a geometric second longitudinal axis parallel with said geometric first longitudinal axis,
   (b) said coil has an opening for a carrier rod parallel with said geometric second longitudinal axis,
   (c) substantially coaxial with said geometric second longitudinal axis, said second part of said energizing means comprises said carrier rod which is rigid in its longitudinal direction relative to said end portion of said bar device and which is connected in entraining fashion to said bar device,
   (d) said carrier rod carries an upper magnet carrier above said coil and a lower magnet carrier below said coil,
   (e) fixed to each of said magnet carriers are a plurality of rigid permanent magnets each having one pole that points axially in the same direction, and
   (f) the travel of said carrier rod amounts to a few millimeters.

2. Instrument according to claim 1, wherein said coil is an air-core coil.

3. Instrument according to claim 2, wherein said coil comprises 1000 to 2000 turns of copper wire less than 1 mm in diameter.

4. Instrument according to claim 3, wherein said coil is designed for currents at least in the range from 0.5 amps to 40 uA.

5. Instrument according to claim 1, wherein said coil is embedded in a solid rigid transverse yoke having two oppositely disposed marginal portions connected each to a solid column, said columns having ends rigidly connected with said housing, and this arrangement is virtually rigid for the measurement forces which occur.

6. Instrument according to claim 5, wherein said transverse yoke is non-magnetizable.

7. Instrument according to claim 5, wherein said columns are non-magnetizable.

8. Instrument according to claim 1, wherein said first and second longitudinal axes are aligned with each other.

9. Instrument according to claim 1, wherein said carrier rod is composed of light metal.

10. Instrument according to claim 1, wherein said carrier rod forms a continuation of said end portion of said bar device.

11. Instrument according to claim 1, wherein each of said magnet carriers has top and bottom ends and carries said like-poled permanent magnets both at said top end and said bottom end.

12. Instrument according to claim 1, wherein all of said permanent magnets are the same and each of said magnet carriers has the same magnetic force.

13. Instrument according to claim 12, wherein the number of permanent magnets is the same on all magnet carriers.

14. Instrument according to claim 1, wherein said permanent magnets are of the KOERMAX type (registered trade mark of Messrs. Friedrich Krupp GmbH).

15. Instrument according to claim 1, wherein said permanent magnets have a diameter in the region of 6 mm, a height in the region of 2 mm and two sets of four magnets each are provided on each of said magnet carriers.

16. Instrument according to claim 1, wherein said magnet carriers have depressions matching said permanent magnets in shape, and over a part of their height said permanent magnets are glued into said matching depressions and the glue is a cold hardening adhesive.

* * * * *